United States Patent

Casavant

(10) Patent No.: US 11,309,058 B2
(45) Date of Patent: Apr. 19, 2022

(54) MODELING THE CHEMICAL COMPOSITION OF A BIOLOGICAL CELL WALL

(71) Applicant: X Development LLC, Mountain View, CA (US)

(72) Inventor: Nicholas Casavant, Palo Alto, CA (US)

(73) Assignee: X Development LLC, Mountain View, CA (US)

(*) Notice: Subject to any disclaimer, the term of this patent is extended or adjusted under 35 U.S.C. 154(b) by 1056 days.

(21) Appl. No.: 15/942,339

(22) Filed: Mar. 30, 2018

(65) Prior Publication Data

US 2019/0303533 A1 Oct. 3, 2019

(51) Int. Cl.
*G16B 5/00* (2019.01)
*G16B 15/00* (2019.01)
*G16C 20/00* (2019.01)
*G16B 5/30* (2019.01)

(52) U.S. Cl.
CPC ............... *G16B 5/00* (2019.02); *G16B 15/00* (2019.02); *G16C 20/00* (2019.02); *G16B 5/30* (2019.02)

(58) Field of Classification Search
CPC . G16B 5/00; G16B 5/30; G16B 99/00; G16B 15/00; G16C 20/00
See application file for complete search history.

(56) References Cited

U.S. PATENT DOCUMENTS

2004/0048264 A1* 3/2004 Stoughton ............... C40B 30/04 435/6.12
2017/0235914 A1 8/2017 Hoeng et al.

FOREIGN PATENT DOCUMENTS

WO 2005/111905 A2 11/2005
WO WO 2014/015196 A2 1/2014

OTHER PUBLICATIONS

Dyson, R. J., L. R. Band, and O. E. Jensen. "A model of crosslink kinetics in the expanding plant cell wall: yield stress and enzyme action." Journal of theoretical biology 307 (2012): 125-136. (Year: 2012).*
Barbacci, Adelin, Marc Lahaye, and Vincent Magnenet. "Another brick in the cell wall: biosynthesis dependent growth model." PLoS One 8, No. 9 (2013): e74400. (Year: 2013).*

(Continued)

*Primary Examiner* — Jesse P Frumkin
(74) *Attorney, Agent, or Firm* — Kilpatrick Townsend & Stockton LLP

(57) ABSTRACT

Techniques are described for determining the strain on a cell wall using two models: 1) a short timescale model, describing the relationship between physical properties assumed to be fixed and 2) a long timescale model, describing the dynamic chemical composition of a cell wall. Short term modeling of the physical properties in a cell wall is used to properly understand how physical factors such as osmotic pressure affects the strain on the cell wall, which is in turn used to identify conditions under which a cell wall will cease to function properly or lyse entirely. Although temporally the physical properties which cause cell walls to underperform/lyse can be evaluated under a short time frame, the chemical properties that lead to the physical properties which cause that behavior themselves change over much longer timescales, in a relative sense.

20 Claims, 11 Drawing Sheets

Example Implementation for Modeling Cell Wall Composition 400

(56) References Cited

OTHER PUBLICATIONS

Chen, Xuewen, Ana P. Alonso, and Yair Shachar-Hill. "Dynamic metabolic flux analysis of plant cell wall synthesis." Metabolic engineering 18 (2013): 78-85. (Year: 2013).*
Johari, Surabhi, et al. "Flux Balance Analysis: An Insilico Analysis of *Staphylococcus aureus* Cell Wall Biosynthesis Pathway Metabolism." 2013 International Conference on Machine Intelligence and Research Advancement. IEEE, 2013. (Year: 2013).*
Wolkenhauer, Olaf, Peter Wellstead, Kwang-Hyun Cho, Jörg Schaber, and Edda Klipp. "Short-term volume and turgor regulation in yeast." Essays in biochemistry 45 (2008): 147-160. (Year: 2008).*
International Report on Patentability dated Oct. 15, 2020 in related application No. PCT/US2018/064128, all pgs.
Bruce, "Mathematical Modelling of the Cellular Mechanics of Plants", Philosophical Transactions of the Royal Society of London. Series B, Biological Sciences, vol. 358, No. 1437, Jul. 30, 2003, pp. 1437-1444.
Dada et al., "Multi-scale Modelling and Simulation in Systems Biology", Integrative Biology, vol. 3, No. 2, Jan. 6, 2011, pp. 86-96.
Endy et al., "Modelling Cellular Behaviour", Nature, vol. 409, No. 6818, Jan. 1, 2001, pp. 391-395.
Geitmann et al., "Mechanics and Modeling of Plant Cell Growth", Trends in Plant Science, vol. 14, No. 9, Sep. 1, 2009, pp. 467-478.
He et al., "Constructing Metabolic Networks Based on Bipartite Model Within Matlab", Computer and Communication Technologies in Agriculture Engineering (CCTAE), Jun. 12, 2010, pp. 330-332.
Hong et al., "Molecular Modeling and Simulation of *Mycobacterium tuberculosis* Cell Wall Permeability", Biomacromolecules, vol. 5, No. 3, May 1, 2004, pp. 1066-1077.
PCT/US2018/064128, "International Search Report and Written Opinion", dated Apr. 30, 2019, 16 pages.
Regev et al., "Cellular Abstractions: Cells as Computation", Nature, vol. 419, Sep. 26, 2002, 343 page.
Rose et al., "Pharmacodynamic Effect of Clinical Vancomycin Exposures on Cell Wall Thickness in Heterogeneous Vancomycin-intermediate *Staphylococcus aureus*", Journal of Antimicrobial Chemotherapy, vol. 65, No. 10, Aug. 6, 2010, pp. 2149-2154.
Walker et al., "The Virtual Cell—a Candidate Co-ordinator for 'middle-out' Modelling of Biological Systems", Briefings in Bioinformatics, vol. 10, No. 4, Mar. 17, 2009, pp. 450-461.
Yi et al., "Architecture-Based Multiscale Computational Modeling of Plant Cell Wall Mechanics to Examine the Hydrogen-Bonding Hypothesis of the Cell Wall Network Structure Model", Plant Physiology, vol. 160, No. 3, Aug. 27, 2012, pp. 1281-1292.

\* cited by examiner

*Example Implementation for Modeling Cell Wall Composition 400*

*Example Implementation for Reaction Classification Module 510*

*Flowchart for Long Timescale Model Analysis 500*

*Flowchart for Short Timescale Analysis*
*600*

*Example Relationship between Stress and Physical Properties*
*675*

MODELING THE CHEMICAL COMPOSITION OF A BIOLOGICAL CELL WALL

BACKGROUND

Field of Art

This description generally relates to biological cell modeling, and specifically physical models for determining the physical properties of a biological cell wall.

Description of the Related Art

Antibiotics are a type of antimicrobial drug that kill or inhibit the growth of bacteria and are used in the treatment and prevention of bacterial infections. Many antibiotics act on the cells wall by inhibiting synthesis of different chemical components of the cell wall, such as membrane lipid bilayers enclosing the cell wall and the peptidoglycans that provide the membrane with structural integrity. Since bacterial cell walls are built by linking molecules together, antibiotics that prevent these cross-links from forming prevent the cell wall from forming altogether, cause the cell wall to form incompletely with porous openings in the cell wall, or prevent the cell from growing and dividing altogether. As a result, ions, proteins, and other biological molecules leak out of or into the cell resulting in detriments to the cell, for example disruption to the protein gradient for energy generation, loss of strength in the cell wall, and ultimately cell death. Additionally, the movement of biological molecules into a cell through a more porous membrane, causes water to flow from the hypotonic environment into the hypertonic cell. Without the presence of the cell wall to resist the increase in osmotic pressure within the interior of the cell, the cell lyses.

SUMMARY

This description provides techniques for computationally predicting the effects of changes in the biochemical reactions within a cell on the resulting physical properties of a biological cell wall. Among other benefits, this facilitates the ability for scientists and researchers to develop more effective medication for treating bacterial infections. More generally, these techniques provide a rapid and inexpensive way for identifying and evaluating novel targets for developing new drugs by reducing the amount of in vivo research needed to evaluate those targets and drugs. Conventional techniques performed in a laboratory setting are often expensive and require significant time to prepare specimens and to interpret the results of the experiments. In contrast, computationally simulating such experiments in silica provides a more efficient and cost-effective approach to performing these experiments and interpreting their results.

Methods are described for determining the strain on a cell wall using two models: 1) a short timescale model, describing the relationship between physical properties assumed to be fixed and 2) a long timescale model, describing the dynamic chemical composition of a cell wall. Short term modeling of the physical properties in a cell wall is used to properly understand how physical factors such as osmotic pressure affects the strain on the cell wall, which is in turn used to identify conditions under which a cell wall will cease to function properly or lyse entirely. Although temporally the physical properties which cause cell walls to underperform/lyse can be evaluated under a short time frame, the chemical properties that lead to the physical properties which cause that behavior themselves change over much longer timescales, in a relative sense.

Regarding those chemical properties, because cells are constantly producing new chemicals and incorporating these new chemicals into the cell wall over time, the changes in the chemical composition of the cell wall are observed using the model of long timescale model. The model of long timescale model records reactions that occur within the cell wall and computationally analyzes those reactions to characterize the chemical composition of: 1) the reactants and products of the reactions and 2) the cell wall that integrates one or more of the products of the reaction. Based on experimentally measured data regarding physical properties of the cell wall, the long timescale model records correlations between changes in the chemical composition of the cell wall and its physical properties.

Using the information determined by the long timescale model, the short timescale model describes the physical properties for a cell wall of a fixed chemical composition by drawing a mechanistic correlation between the osmotic pressure and other physical properties within a cell and the material stress experienced by the cell wall. By manipulating input values for any of these physical properties, the short timescale model provides greater insight into mechanics of the strain experienced by the cell wall.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION OF DRAWINGS

I. Simulation Model of a Simulation System

Figure 1:
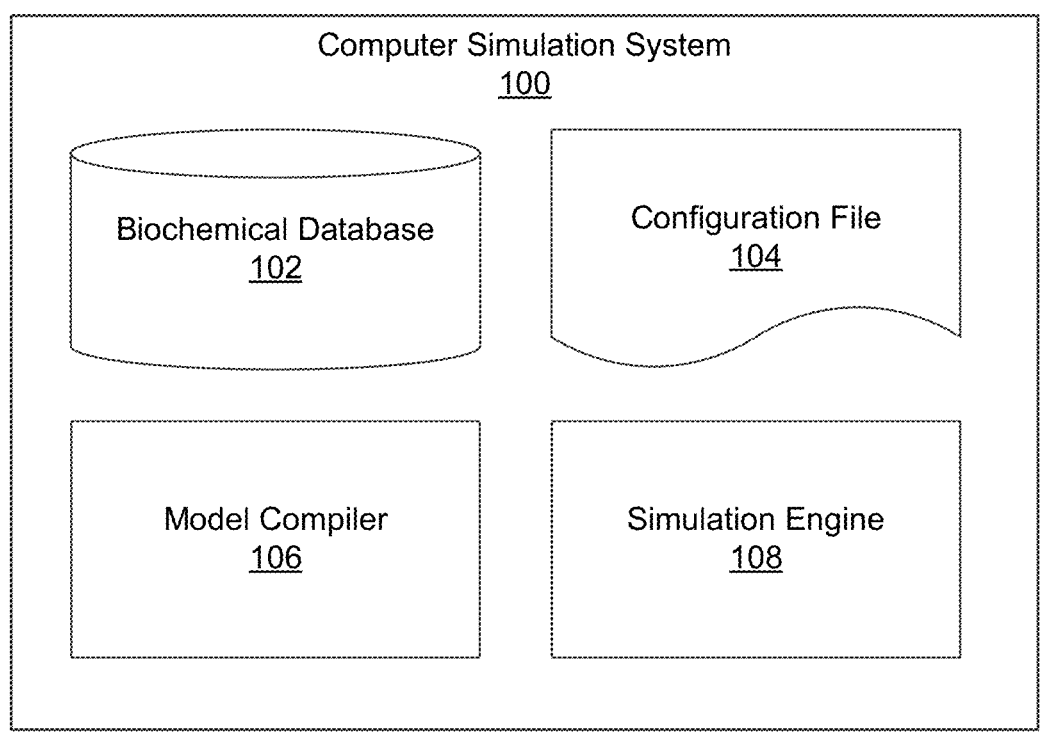
FIG. 1 is a block diagram illustrating computation components of a simulation system for modeling the behavior of a biological cell, in accordance with an embodiment.

FIG. 1 is a block diagram illustrating computational components of a computer simulation system 100 (herein referred to as simply "simulation system") for modeling the behavior of a biological cell, in accordance with an embodiment. The simulation system 100 may be organized into four separate computational components, although other implementations may include fewer or greater numbers of computational components. Depending on the embodiment, each component of the simulation system 100 may implemented on one or more servers or other computational devices that are configured to communicate over a network (e.g. the Internet, a local area network, etc.). Alternatively, all computational components may be locally present on a single computational device. The four computational components comprising the simulation system 100 shown in FIG. 1 are a biochemical database 102, a model configuration file 104, a model compiler 106, and a simulation engine 108.

Figure 3:
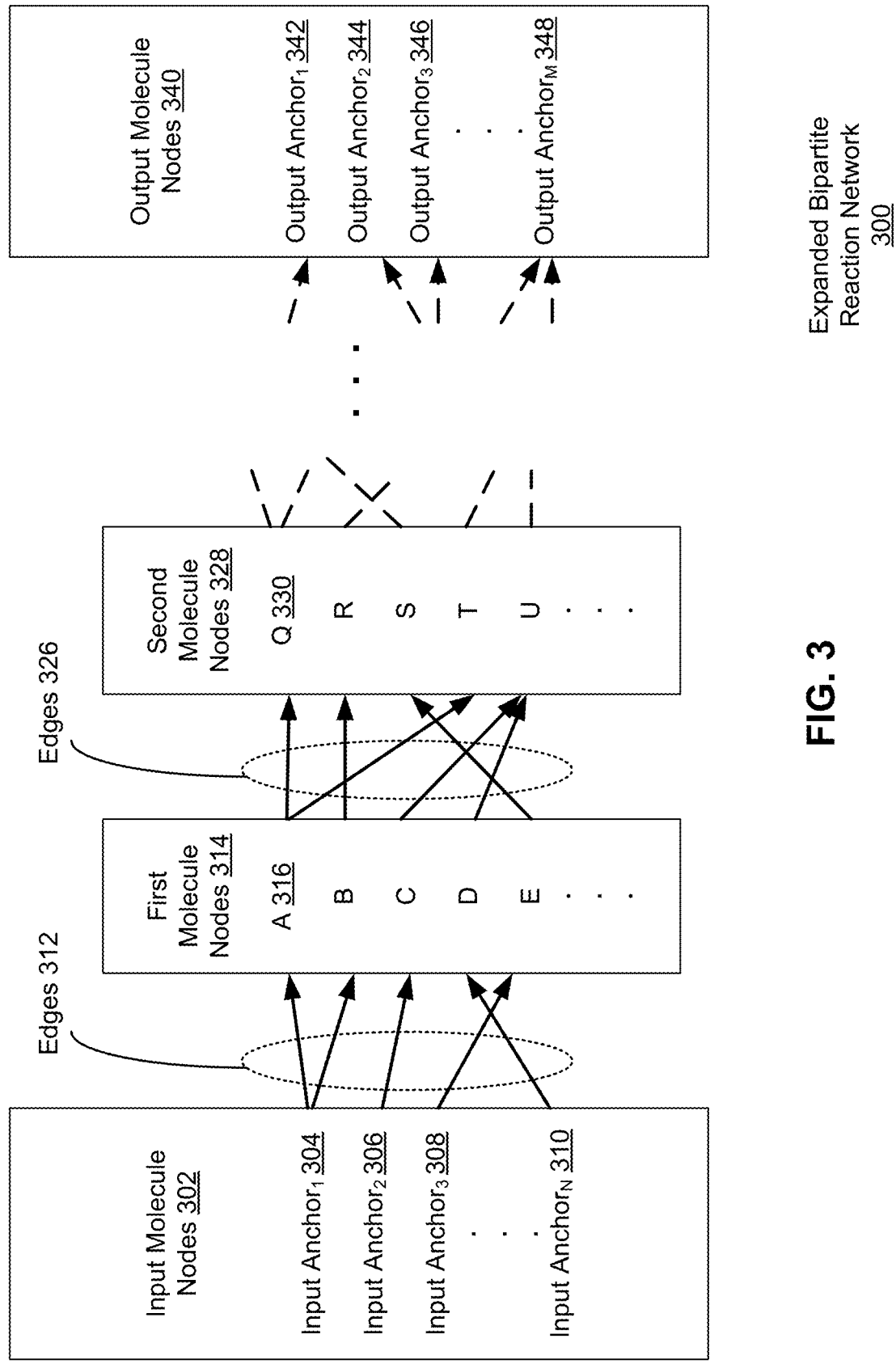
FIG. 3 is a block diagram illustrating a cell reaction network structured as a bipartite graph, according to an embodiment.

The biochemical database 102 is a database that stores data on molecules and processes that may be present or may occur in a biochemical environment simulated using the simulation system 100. The biochemical database 102 stores compositional data for each molecule that may be of use in the simulation, as well as data specifying how each molecule may be involved in one or more processes simulated by the simulation system 100. Although any database structure may be used to implement the biochemical database 102, FIG. 3 illustrates an a reaction network 300 implemented in this exemplary description as a bipartite biochemical database as that may be used in the simulation system 100 as the biochemical database 102. Those of skill in the art will recognize that the same biochemical information stored in the specified reaction network 300 could be stored in another type of biochemical database 102.

The configuration file 104 is a set of instructions for configuring the simulation system 100. The simulation system 100 may be configured to simulate a single set of molecules and processes and, therefore, is not configured separately for each use of simulation system 100. Alternately, the configuration file 104 is used to select the molecules and processes to be simulated in the simulation system 100, and is therefore configured separately for each use of the simulation system 100. Additionally, the configuration file 104 may designate the specific cell functions to be modelled as well as the models to be included in the simulation system 100. Furthermore, the configuration file 104 may include parameters for the Flux Balance Analysis (FBA) and the models included in the simulation system 100, as well as a set of initial conditions for each of those models.

The model compiler 106 uses configuration file 104 to compile the simulation system 100 so that simulations can be run. The model compiler 106 accesses the data retrieved from the biochemical database 102 and the configuration file 104 to generate various components of each simulation, examples of which include but are not limited to: a stoichiometric matrix, a bipartite network link molecule and process nodes, initial flux vectors and quantities prior to a model being run for the first iteration, an objective function for each model, and any constraints on any of the models.

The simulation engine 108 performs the calculations required to simulate a biochemical process using the simulation system 100. The simulation engine 108 may initialize a given simulation using the initial conditions as constructed by the compiler 106. The simulation engine 108 creates an initial state vector, which includes the concentration of each molecule included in the simulation. The simulation engine 108 creates any initial exchange flux values into and out of each model in the simulation. The simulation engine 108 then iterates through a time step of the simulation, running the models of the simulation with the input state vectors and fluxes. Generally, this involves the simulation engine 108 arriving at a solution of the model for a first time step after the initial state, where the time step is of a predetermined length. The solution for each model for that time step may include, but is not limited to, the concentrations of the molecules output by each model, the fluxes of those molecules, and any changes to the overall biochemical environment (e.g. temperature changes, pH changes, etc.) caused by the processes being simulated by each model.

After the completion of the initial time step of the simulation, the simulation engine 108 updates the initial state vectors, flux vectors, and any other relevant state vectors with the output of the initial time step. As a specific example, the simulation engine 108 may use the fluxes determined during the running of the models multiplied by the length of the predetermined time step to determine the new concentrations of the molecules included in the models of the simulation. As another specific example, the simulation engine 108 may also calculate the exchange fluxes that connects each model with each other model in the simulation. The simulation system 100 then runs a second time step of the simulation similarly to the first time step using the updated state vectors and any other parameters of the simulation. The simulation engine 108 continues this process for a number of time steps or until reaching a termination state or receiving a termination input.

II. Sub-Models in Cell Modeling

Figure 2:
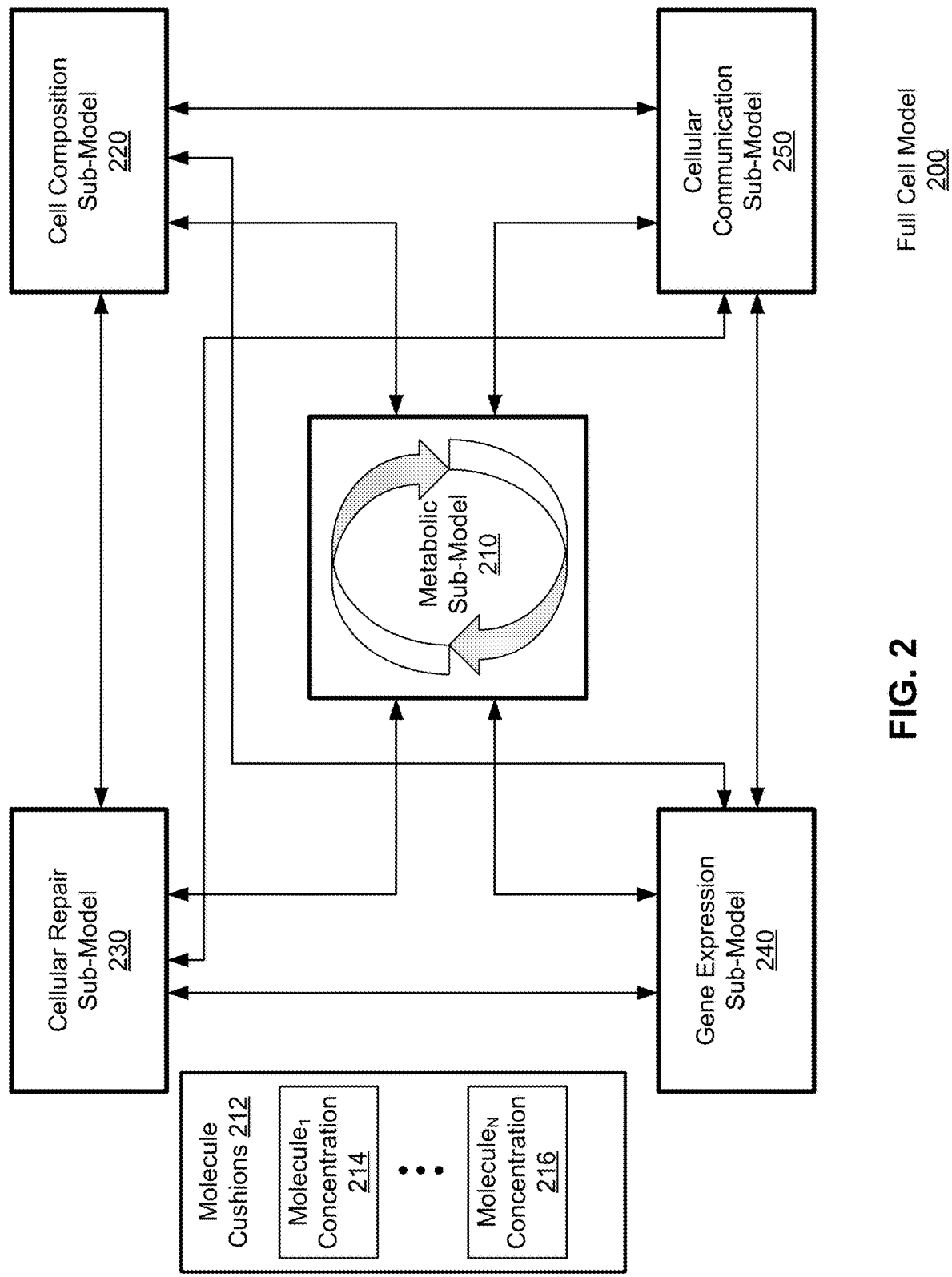
FIG. 2 is a block diagram illustrating a full cell model, according to an embodiment.

FIG. 2 is a block diagram of a full cell model 200, according to one embodiment. The full cell model 200 contains a cellular metabolic sub-model 210 with any number of sub-models which input and/or output with other sub-models or the cellular metabolic sub-model 210. The sub-models include the cellular repair sub-model 230, the cell composition sub-model 220, the gene expression sub-model 240, and/or the cellular communication sub-model 250. The arrows leading to the cellular metabolic sub-model 210 represent the input flux and/or output flux values between the cellular metabolic sub-model 210. Arrows between sub-models and cellular metabolic sub-model 210 may also represent the supply of molecules from these sub-models to cellular metabolic sub-model 210.

As shown in FIG. 2, arrows lead from sub-models into cellular metabolism 306 and from cellular metabolic sub-model 210 into sub-models. This is an illustration of the fact that many cellular processes contain molecules and reaction pathways that are both inputs into cellular metabolic sub-model 210 and which are produced by cellular metabolic sub-model 210. Thus the sub-models shown in FIG. 2 may be both upstream sub-models and downstream sub-models, as described with reference to FIG. 1. The interactions between sub-models and cellular metabolic sub-model 210 may be coordinated by a single dataset that aggregates changes within the full cell model 200, such that each of the sub-models and cellular metabolism 306 receive and transmit information to the single dataset, rather than to each other. This single dataset may be a state dataset, and is described in further detail with reference to FIG. 3.

In addition to molecule concentrations within sub-models and cellular metabolic sub-model 210, the full cell model 200 may include molecule cushions 212 that exist outside of system of supply and demand between the sub-models and cellular metabolic sub-model 210. The molecule cushions 212 represent reserves of molecules within the cellular environment. For example, molecule cushions 212 may be molecules that exist within a cell's cytoplasm, and which are available to molecular processes when needed. Molecule cushions 212 contain different reserve concentrations of different molecules. For example, a first molecule, molecule$_1$, may have a concentration molecule$_1$ concentration 214. If molecule$_1$ is a molecule that has a large flux value or demand within the system of sub-models and cellular metabolic sub-model 210, then the reserve concentration of molecule$_1$ may be larger than other molecules with smaller demand. Thus the concentration of molecules within molecule cushions 212 may be proportional to the flux value associated with the molecule in cellular metabolism, the aggregate demand for the molecule within the sub-models, and/or any other measurement of demand within the system of sub-models and cellular metabolic sub-model 210. The molecule cushions 212 ensure that sudden increases in demand for a molecule within the full cell model 200 do not result in complete depletions of a molecule within the full cell model 200.

There may be any number of molecules within molecule cushions 212. A total of N molecules, represented by molecule$_N$ concentration 214, are assigned reserve concentrations within molecule cushions 212. In some examples, all molecules within the full cell model 200 are assigned reserve concentrations within molecule cushions 212. In other examples, molecules with demand and/or flux values above a threshold are assigned reserve concentrations within molecule cushions 212, such that a subset of the molecules within the full cell model 200 representing the primary flow of molecules are stored in molecule concentrations molecule$_1$ concentration 214 through molecule$_N$ concentration 216.

The effect of the molecule cushions 212 on the full cell model 200 is that the molecule cushion concentrations allow the demand for a molecule to instantaneously (e.g., for a given single time step evaluating the subunits) exceed supply without disrupting the full cell model 200. This allows the production network to continue to function as a demand load is applied to the system of the full cell model 200, giving the cell time to increase production of the molecule to meet the new demand.

III. Reaction Network for Cell Modeling

FIG. 3 is a block diagram illustrating a cell reaction network 300, structured in an exemplary embodiment as a bipartite graph. The reaction network 300 includes input molecule nodes 302. The input molecule nodes 302 represent the input molecules of a given cell process (e.g., as implemented within the simulation system 100 by one of several sub-models, as discussed with respect to FIG. 2 above), and are the input boundary of the reaction network 300 of either the entire cell or some portion thereof if the network is created for a specific cell process. Each of the input molecule nodes 302 is connected to at least one process node to form a bipartite graph of connected molecule nodes and process nodes (not shown). In this structure, molecule nodes are connected by edges to the process nodes of the biochemical reactions they are involved in, which are in turn linked by edges to the molecule nodes they create, and so on. For simplification in FIG. 3, the process nodes and the edges linking process nodes to molecule nodes have been condensed and are shown and referred throughout as edges connecting molecule nodes. It is to be understood that the edges described herein are stored within a bipartite graph as process nodes with edges connecting each molecule node to its associated process nodes.

Thus as in the prior paragraph, in the example of FIG. 3 each of the input molecule nodes 302 is connected to at least one of the first molecule nodes 314 with edges 312. The first molecule nodes 314 represent the first products of. The first molecule nodes 314 may be connected to the second molecule nodes 328 with edges 326. Depending on the number of molecule nodes in the reaction network 300, there may be any number of additional molecule nodes and edges. Finally, the output molecule nodes 340 represent the outputs of a given model within the simulation, and are the output boundary of the reaction network 300.

III.A Scope of the Bipartite Network

The reaction network 300 includes all molecules, reactions and reaction pathways that are used in a steady-state mathematical simulation of a cell. For example, the reaction network 300 contains all molecules, reactions and reaction pathways used in a metabolic sub-model 210, a cell wall composition sub-model 220, etc.

III.B Molecule Nodes

As described herein, within a cell reaction network structured as a bipartite graph, molecule nodes, such as molecule nodes 302, first molecule nodes 314, second molecule nodes 328, and output molecule nodes 340 are nodes of the bipartite graph that represent a molecule or chemical element that is present in a reaction within a cell. A molecule node may represent small molecules such as water, carbon dioxide, protons, etc. or macromolecules such as proteins, lipids, alcohols, organic acids, vitamins, etc. As stored in the reaction network 300, a molecule node may contain a plurality of metadata fields describing the molecule. The metadata of a molecule node may include the molecule name, a molecule formula, a monomer sequence, a macromolecular structure, electrical charge, chemical or physical properties (pKa, melting point, solubility, etc.) and any component molecules. Additionally, some non-physical properties may be included in the metadata of a molecule node including drug interaction, 3D structure etc. A molecule node need not contain information for each one of the previously described metadata categories.

III.C Input Notes

Input molecule nodes 302 represent molecules that are inputs to cell reactions, and thus to the reaction network 300. The input molecule nodes 302 include molecules that are inputs to cell reactions from an upstream cellular process, as well as molecules in the cytoplasm of a cell, and molecules that the cell model is capable of sourcing from its external environment and using in a cell reaction network. All of the input molecule nodes 302 and input anchors have an input flux value solution. The input flux value solutions for the input molecule nodes 302 may be determined by solving one or more of the models of the simulation using the other molecules and reactions of the reaction network 300. The input flux value solution for a molecule node in the reaction network 300 represents the rate at which that molecule enters the cell reaction network at steady state. The input flux of a molecule node can be conceptualized as the "demand" for the molecule by the model. In some examples, the flux value solutions of all input anchors and input molecule nodes 302 are non-zero. In other examples, input flux value solutions for a subset of the input molecule nodes 302 and input anchors are 0.

Molecules that are input molecule nodes 302 are "anchored" within the reaction network 300 and stored within the input molecule nodes 302 as input anchor$_1$ 304, input anchor$_2$ 306, input anchor$_3$ 308 through input anchor$_N$ 310, where N is the total number of input molecule nodes 302. As used herein, "anchored" nodes (such as input anchor$_1$ 304, input anchor$_2$ 306, input anchor$_3$ 308 through input anchor$_N$ 310) are molecule nodes that are always included in FBA analysis of the reaction network 300. As described above the molecules represented by the input anchors input anchor$_1$ 304, input anchor$_2$ 306, input anchor$_3$ 308 through input anchor$_N$ 310 need not be present within the cell during mathematical simulations using the reaction network 300.

In an example, the input anchor$_1$ 304 represents a molecule that is a direct input to a particular reaction of the cell from an upstream cellular process. For example, the upstream cellular process may be transcription, such that the input anchor$_1$ 304 molecule is an RNA molecule previously used in the cell and that is then broken down in the cell. The input anchor$_1$ 304 has an input flux value solution, as calculated from a mathematical model of the reaction network 300, such as an FBA model for metabolism. Input anchor$_1$ 304 is thus at the "boundary" to the reaction network 300, and enters the reaction network 300 at a rate given by its input flux value solution, representing the rate of consumption of RNA.

In another example, the input anchor$_2$ 306 is also a direct input to a reaction within the cell, however it is not present within an upstream cellular process and is instead sourced by the cell through a membrane transport pathway, or some other cellular mechanism. The input anchor$_2$ 306 may not have a concentration within the cell during mathematical simulation of the reaction network 300. Alternatively, the input anchor$_2$ 306 may be present in the environment outside of the cell, and through a membrane transport pathway, the cell delivers the input anchor$_2$ 306 to the reaction network 300. The input anchor$_2$ 306 may contain metadata linking it to the membrane transport pathway, or other cellular mechanism from which it is sourced to the reaction network 300.

In another example, the input anchor$_3$ 308 may have a constant or near-constant presence within the cytoplasm of the cell, such that the molecule of the input anchor$_3$ 308 is stored at some concentration external to the cell reaction network, but within the cell model. The input flux of the input anchor$_3$ 308 thus represents a movement of the input anchor$_3$ 308 from the cell's storage concentration to the reaction network 300.

III.D Process Nodes Shown as Edges

The process nodes and edges linking molecule nodes to process nodes in a bipartite graph are shown and referred to throughout as edges for simplification. As referred to throughout, each edge is a process node in the bipartite graph with connecting edges to its associated molecule nodes. Edges 312 connect input molecule nodes 302 to first molecule nodes 314. Specifically, a single edge 312 connects a single input molecule node 302 to a single molecule node in the first molecule nodes 314. Each edge in the edges 312 represents a chemical reaction or process converting the input molecule to a molecule in the first molecule nodes 314. For example, as shown in the reaction network 300, the input anchor$_1$ 304 is connected by an edge in the edges 312 to molecule A 316 in the first molecule nodes 314. This edge represents a chemical reaction or process in which the input anchor$_1$ 304 is a reactant, and molecule A 316 is a product.

The direction of the edges 312 (e.g., pointing from input molecule nodes 302 to first molecule nodes 314) indicates the direction of the chemical reaction. Thus an edge pointing from a first molecule to a second molecule indicates that the first molecule is a product and the second molecule is a reactant in the chemical reaction. As described herein, an edge "leading out" of a molecule node indicates that the chemical reaction uses that molecule as a reactant, and that the direction of the chemical reaction in the cell reaction network is forward, away from that molecule. As described herein, an edge "leading into" a molecule node indicates that a chemical reaction produces that molecule as a product, and that the direction of the chemical reaction in the cell reaction network is forward toward that molecule. For example, edges 312 lead out of the input molecule nodes 302 and lead into the first molecule nodes 312. Specifically, an edge in the edges 312 leads out of input anchor$_1$ 304 and into molecule A 316 of the first molecule nodes 314.

The reaction network 300 then includes second molecule nodes 328, which are shown connected to first molecule nodes 314 with edges 326. The first molecule nodes 314 may be reactants in chemical reactions that produce second molecule nodes 328 as products. The edges 326 indicate which of the first molecule nodes 314 are converted to second molecule nodes 328, as well as the direction of the chemical reactions. Not all of the first molecule nodes 314 may be converted to second molecule nodes 328. This may be due to some of the first molecule nodes 314 and/or second molecule nodes 328 being unused or unmade molecule nodes. In some examples, some of the second molecule nodes 328 may be reactants in chemical reactions that produce the first molecule nodes 314 as products, such that the edges 326 lead out of these second molecule nodes 328 and into the first molecule nodes 314. This may be due to cyclical portions of the reaction network 300.

Edges 312 and 326 may store metadata further specifying the details of the chemical reactions within the reaction network 300. For example, edges 312 and 326 include the stoichiometric balance between the two molecules they are connected to. The edge connecting molecule A 316 and molecule Q 330 includes the stoichiometry of the reaction converting molecule A 316 to molecule Q 330. The edges 312 and 326 may also include the enzymes, cofactors, or other facilitating molecules involved in a chemical reaction. Edges 312 and 326 may include protein folding operations and the movement of these facilitating molecules in the cell, as well as rates and locations and numbers of active sites. Additionally or alternatively, edges 312 and 326 store activation energy, Gibbs free energy change, kinematic properties and other thermodynamic properties known in the art describing the chemical reaction. Edges 312 and 326 may store this and any additional information relevant for describing the chemical reactions or processes that convert molecule nodes from reactants to products within the reaction network 300.

Edges 312 and 326 have associated flux values, which are rates at which molecule nodes are converted from reactants into products, however, since these edges are not at the boundaries of metabolism, they may not be solved for in an FBA model using the reaction network 300. The direction of flux through the reaction network 300 and between molecule nodes in indicated by the direction of the edge. For example, the edge leading out of molecule A 316 and into molecule Q 330 has an associated flux rate, which indicates the rate at which molecule A 316 is converted into molecule Q 330.

The flux values of the input anchors are the input flux values of the reaction network 300, and may be determined through a mathematical simulation of the reaction network 300, such as an FBA model simulation.

III.D Output Nodes

There may be any number of molecule nodes within the reaction network 300. Ultimately, the reaction network 300 ends with the output molecule nodes 340. Output molecule nodes include any number of output anchor molecules, such as output $anchor_1$ 342, output $anchor_2$ 344, output $anchor_3$ 346 through output $anchor_M$ 348, where M is the total number of output molecules of the reaction network 300. Each of the output molecule nodes 340 represent the outputs of metabolism as shown as the reaction network 300. The output molecule nodes 340 may thus be used in cellular processes downstream from metabolism, stored within the cell, output through a membrane transport pathway, and/or any other use in the cell external to metabolism. Each of these cellular processes may have their own associated mathematical model and simulation.

All of the output molecule nodes 340 and output anchors have an output flux value solution. The output flux value solutions for the output molecule nodes 340 may be determined by solving an FBA model using the reaction network 300. The output flux value solution for a molecule node in the reaction network 300 represents the rate at which that molecule leaves the network at steady state. The output flux of a molecule node can be conceptualized as the metabolic "production" of the molecule. In some examples, the flux value solutions of all output anchors and output molecule nodes 340 are non-zero. In other examples, output flux value solutions for a subset of the output molecule nodes 340 and output anchors are 0.

Each of the output molecule nodes 340 are designated as "anchored" nodes. Thus output $anchor_1$ 342, output $anchor_2$ 344, output $anchor_3$ 346 through output $anchor_M$ 348 are isolated from the rest of a reaction network 300 when the reaction network 300 is simplified and condensed. Not all of the output anchors need be produced during a given simulation of the reaction network 300, however at least one reaction pathway within the reaction network 300 must be capable of producing the output molecule nodes 340 as its final product. Thus at least one edge in the bipartite network leads into each of the output molecule nodes 340.

Input molecule nodes 302, first molecule nodes 314, second molecule nodes 328, and output molecule nodes 340 may each be stored as arrays, or in any other data structure known in the art. Input molecule nodes 302, first molecule nodes 314, second molecule nodes 328, and output molecule nodes 340 may be different dimensional arrays, and thus need not have the same number of components. Input molecule nodes 302, edges 312, first molecule nodes 314, edges 326, second molecule nodes 328, and output molecule nodes 340 are populated into the reaction network 300 as molecule nodes connected to process nodes from a variety of sources, such as primary literature, databases, biochemistry textbooks, conference presentations, or any other primary source literature. As initially input into the reaction network 300, there may be redundancies in the reaction network 300, or reaction pathways between molecule nodes that are dead-ends, such that at steady state of the reaction network 300, there is zero flux through the pathway. The biochemical relation between all molecules within a reaction network is thus converted to a structure of reaction edges (e.g., process nodes) and connected molecule nodes to form the reaction network 300. To identify features of the reaction network, such as the relative importance of reaction pathways, or dead-end pathways, one can analyze the structure of the reaction network 300. Specifically, the biochemical relation of each molecule and its corresponding molecule node to other molecules and molecule nodes is given by the edges into and out of each node. By categorizing molecule nodes according to the number of edges into and out of each node, the reaction network 300 can be condensed and simplified, and important reaction pathways identified.

IV. Cell Composition Sub-model

IV.A Overview

Figure 4A:
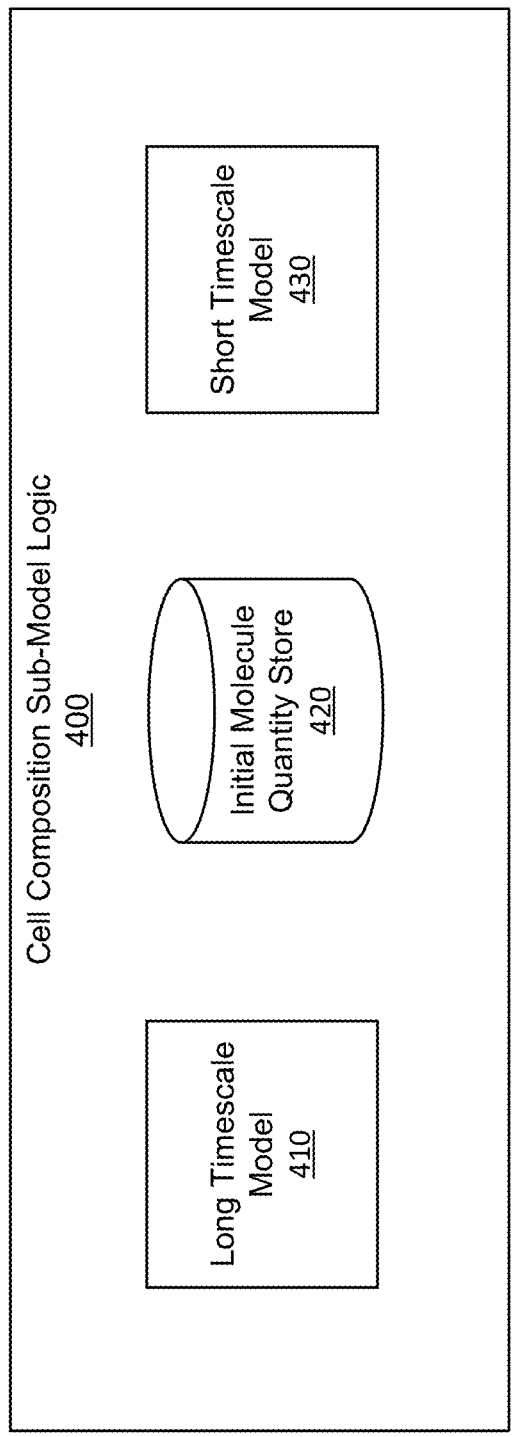
FIG. 4A is a block diagram illustrating the logical architecture of the cell-composition sub-model, according to an embodiment.

FIG. 4A is a block diagram illustrating the logical architecture of the cell-composition sub-model, according to an embodiment. In practice, the computer logic 400 of the cell composition sub-model is configured to determine the relationship between changes in the chemical composition of the cell membrane and resulting changes in the physical properties of the cell membrane. The cell composition sub-model logic 400 comprises a long timescale model 410, an initial molecule quantity store 420, and a short timescale model 430. In other embodiments, the cell composition sub-model logic 400 may include more or fewer modules. Functionality indicated as being performed by a particular module may be performed by other modules instead.

To model changes in cell physical properties based on changes in cell chemical composition effectively, the logic 400 of the sub-model separates data based on the timescale over which different cell processes act. Specifically, changes in the chemical composition of a cell membrane occur over a relatively extended period of time. For example, the prevalence of cell membrane cross-links in the membrane of the cell wall is something that shifts over time (e.g., as measured in tens of minutes) as production of the underlying compounds that make up the cross-links rises and falls. By contrast, changes in the physical properties of cell, such as the porosity of the cell wall, can have short time scale implications (e.g., on the order of seconds), such as the sudden occurrence of cell lysis based on osmotic pressure. The long timescale model 410 and short timescale model 430 of logic 400 are designed to separately handle these timescales, and interact in order to determine the effect on the cell wall.

IV.B. Long Timescale Model Introduction

Figure 4B:
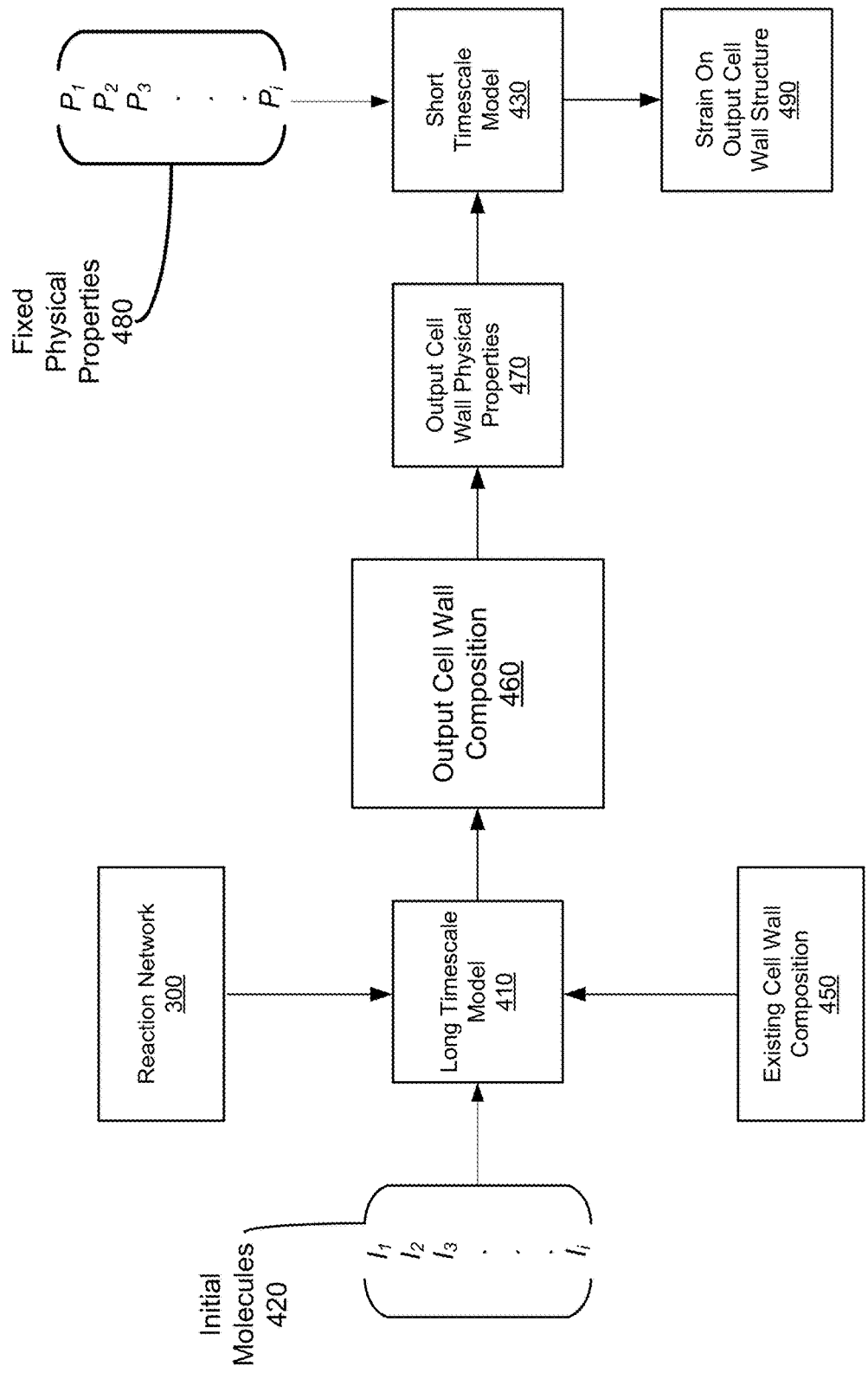
FIG. 4B is a flow chart illustrating the implementation of a long timescale model and a short timescale model to represent the chemical composition of a cell wall, according to an embodiment.

Referring now to FIG. 4B, a flow chart is illustrated describing the implementation of the long timescale model 410 and the short timescale model 430 within logic 400, according to an embodiment. In one embodiment, the long timescale model 410 is a statistical model correlating initial molecule concentrations 420 from reaction network 300, particular reactions 300, and an information known about the existing cell wall molecular composition 450 to determine a change in that cell wall molecular composition 460. For brevity, cell wall molecular composition is shortened simply to "cell wall composition," but refers at least to a set of molecules identified to be relevant to the cell wall's formation, structure, and/or maintenance.

In more detail, the long timescale model 410 access one or more initial molecule concentrations or amounts 420 from store 420 as an input. The long timescale model 410 also access the reaction network 300 to identify reactions that relate to the cell wall. Using the initial molecules 420 as reactants, the long timescale model 420 identifies, from the reaction network 300, a set of reactions involved in cell wall generation/composition and updates each reaction based on the amounts of the reactants used for those reactions, either directly or indirectly through a chain of such reactions. Beyond reactants, the initial molecules 420 may also include amounts of available enzymes involved in the above-identified reactions. Further, beyond molecules 420, the information obtained and input into the long timescale model 410 may also include non-quantity parameters such as, for example, enzymatic or kinetic rates, and the locations or diffusivity of the enzymes within the cell envelope. The long timescale model 410 also accesses an existing cell wall composition 450. Generally, this is information other than the concentrations or amounts of molecules actually making up the cell wall (as that is already contained in the initial molecules 420), such as information that may inform reaction rates or other processes.

Using the initial molecules 420 as reactants, the long timescale model 410 simulates the accessed reactions of the reaction network 300 and determines the estimated output molecules that would result based on the initial molecules 420. Depending on the intermediate steps of the chemical reactions being simulated within the long timescale model 410, several iterations through the reaction network 300 described in reference to FIG. 2 may be required. For example, during the first step of the reaction occurring, the initial molecules 420 may be the input molecule nodes 302 that produce a set of output molecules nodes 340. However, for any subsequent intermediate steps, the input molecules nodes 302 will be updated to be the output molecules nodes produced from the previous step.

The estimated output molecules generated by the long timescale model 410 are used to determine an output cell wall composition 460. This may be represented as an aggregate count and/or determination of the amount/concentration of the molecules that make up the cell wall post-modeling. Further, a change in the cell wall composition may be computed, again in terms of how various molecule counts or concentrations have changed post-model operation. Thus, the long timescale model 410 creates, in silico, an estimation of how a real cell wall would respond to particular initial molecule 420 conditions as a measure of the resulting output molecule concentrations, without the need to perform such an experiment in vivo. Such in silico experimentation allows significantly higher throughput experimentation at lower cost relative to web lab experimentation to obtain these results.

IV.C. Simulations and Output Processing

The description above describes the use of the long timescale model 410 for a single "test", also referred to as a single "simulation." Multiple simulations can be run using model 410 in series or in parallel using different sets of initial molecules 420 along with the specification of other simulation parameters. Example simulation parameters include, but not limited to, types of reactants, amounts/concentrations of reactants, gene mutations, timing, availability of enzymes, and so on. Each simulation is run according to the simulation parameters and according to any one of a number of processing techniques, including but not limited to: stoichiometric mass balance models used with flux based analysis, ordinary differential equation models, partial differential equation models, Monte Carlo simulations, or some combination thereof. The result of each simulation is simulation data which describes the cell's state throughout the simulation. The model cell's state may comprise amount of molecules, reaction rates, and so on. The result of each simulation is simulation data which describes the cell's state throughout the simulation (including through the running of the long timescale model 410 over one or more time steps). As a baseline state, the existing cell wall composition 450 may be considered a control simulation which can be imported or be selected from a previous simulation.

After a simulation is run, the existing cell wall composition 450 may be updated by logic 400 to consolidate the predicted outputs from the long timescale model 410. Generally, molecules added to the cells are proteins. The chemical composition of the cell wall is additionally based on the number of cross-links between the proteins of the cell wall, the chain length describing the number of molecules in the cell wall, the mass of the cell wall, the thickness of the cell wall, the identities of one or more chemical constituents of the cell wall, and the arrangement of the chemical constituents in the cell wall. While some of these items can be directly determined from the output molecules provided by the long timescale model 410, others of these may be derived from those numbers. Mass, thickness, and other similar quantities are examples of this. Further, some aspects of the cell wall composition 450 may be based on information about the type of cell being modeled, for example, a gram negative bacterial cell in which the cell wall lines the exterior of the cell and the cell membrane lines the interior of the cell wall, may involve different molecules or derived concepts thereof relative to a gram positive bacterial cell in which the cell wall rests in between two cell membranes—one interior to the cell and the other exterior to the cell. Logic 400 is configured to perform these additional calculations as needed.

IV.D. Short Timescale Model Introduction

The composition of the cell wall is a dynamic combination of proteins, lipids, carbohydrates, and other biological molecules. As such, the existing cell wall composition 450 is also in state of constant flux depending on the initial molecules 420 available to the processes of a cell involved in creation and maintenance of the cell wall. Additionally, components of the cell wall may not always have a single defined structure. For example, a peptidoglycan used in a cell wall comprises a sugar backbone with crosslinks that's insert into the cell membrane, but do not have a single defined structure. As a result, the existing cell wall composition 450 may be thought of as a mesh with a constantly changing chemical composition and structure.

The output cell wall composition 460 is, at least in part, used to correlate the changes in the chemical composition of the cell wall with the physical properties of the cell wall. For example, the integration of the protein MreB, functionally homologous to the eukaryotic protein actin, governs the synthesis of peptidoglycans which affect the shape of the bacteria cell. Additional physical properties of the cell membrane include, but are not limited to, mechanical stress, mechanical strain, turgor pressure, osmotic pressure, and turgor pressure.

In one embodiment, the long timescale model 410 is used in a number of simulations using various input molecules and other simulation parameters to determine the effect on the output cell wall compositions. For each of these combinations, the output cell wall physical properties 470 are measured, either in silico or in vivo. These measurements of the physical properties 470 are used to determine a short timescale model 430 of the relationship between the output cell wall composition 460 and the output cell wall physical properties 470. In practice, some physical properties 470 will be shown to be variable 460 in view of cell wall composition 460 while others will be shown to be fixed 480. In one embodiment, the short timescale model is a physics/physical model, however in other embodiments may be implemented differently.

In one implementation, the physical properties are measured computationally by running simulated tensile and geometric assessments on output cell wall compositions 460. In another implementation, the physical properties are measured experimentally by recreating an in-vivo version of the output cell wall 360 in a laboratory environment. A variety of techniques may be used to measure and calibrate measurements of physical properties including, but not limited to, a sensor apparatus, an empirical model, and a microfluidic chip. Osmotic pressure readings and other measurements of physical property may be calibrated by short timescale model 430 using experimentally gathered data from a microfluidic chip. By varying the osmolarity of the fluid passing over the chip, observing the changes in cell size due to tonicity, and measuring additional physical properties, relationships may be determined between the identified physical properties that may be incorporated into the design of the physical model.

The short timescale model 430 may then be used to provide measurements of the variable physical properties (such as strain 490) in response to an input cell wall composition 460 and knowledge of values for the fixed physical properties 480. For example, by inputting the fixed physical properties 480 and the output cell wall physical properties 470 into a physics-based model, the short timescale model 430 determines the maximum strain 490 that can be endured by the cell wall. Based on the computed strain value, the short timescale model 430 provides insight regarding the conditions under which the cell will lyse.

V. Long Timescale Model

Figure 5A:
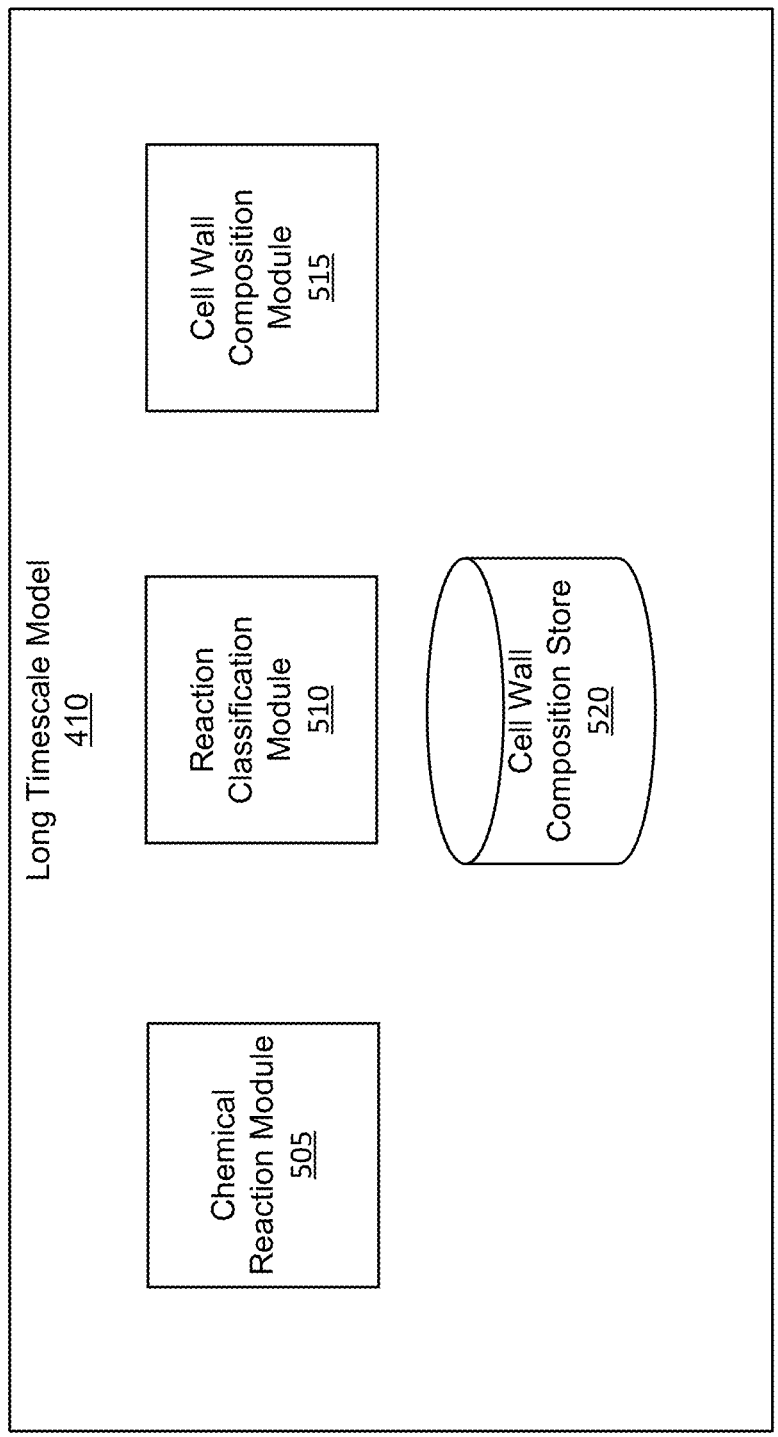
FIG. 5A is a block diagram illustrating the logical architecture of a long timescale model, according to an embodiment.

FIG. 5A is a block diagram illustrating the logical architecture of the long timescale model 410, according to an embodiment. As discussed earlier, the long timescale model 410, first, relates the reactants from a chemical reaction to changes in the chemical composition of the cell wall and, second, relates the changes in the chemical composition of the cell wall to physical properties of the cell wall. In one embodiment, the long timescale model 410 comprises a chemical reaction module 505, a reaction classification module 510, a cell wall composition module 515, a cell wall composition store 520, a physical property analysis module 525, and a physical property store 430. In other embodiments, the long timescale model 410 may include more or fewer modules. Functionality indicated as being performed by a particular module may be performed by other modules instead.

The chemical reaction module 505 accesses the initial molecules 120, simulates the occurrence of the appropriate chemical reactions from network 300 and determines the resulting output molecules 140.

The reaction classification module 510 classifies a reaction into a category of reactions sharing similar reaction rates. The classification may also be assigned to the outputs and/or inputs involved in a reaction. Reactions may also be classified in part based on the type of reaction. In some implementations, for reactions similar to those classified by the reaction classification module 510, the chemical reaction module 505 does not simulate particular reactions, instead referencing a previously classified reaction with similar input molecule nodes 102 and tracing the edges 312 to one or more output molecule nodes 340. Further details regarding the chemical reaction module 505 and the reaction classification module 510 are described in reference to FIG. 5B, described below.

The cell wall composition module 515 receives and processes the products of the simulated reactions and updates the output cell wall composition 460, accordingly. The output cell wall composition 460 along with the structural effects of various types of products (e.g., specific proteins, lipids) are stored within the cell wall composition store 520.

Figure 5B:
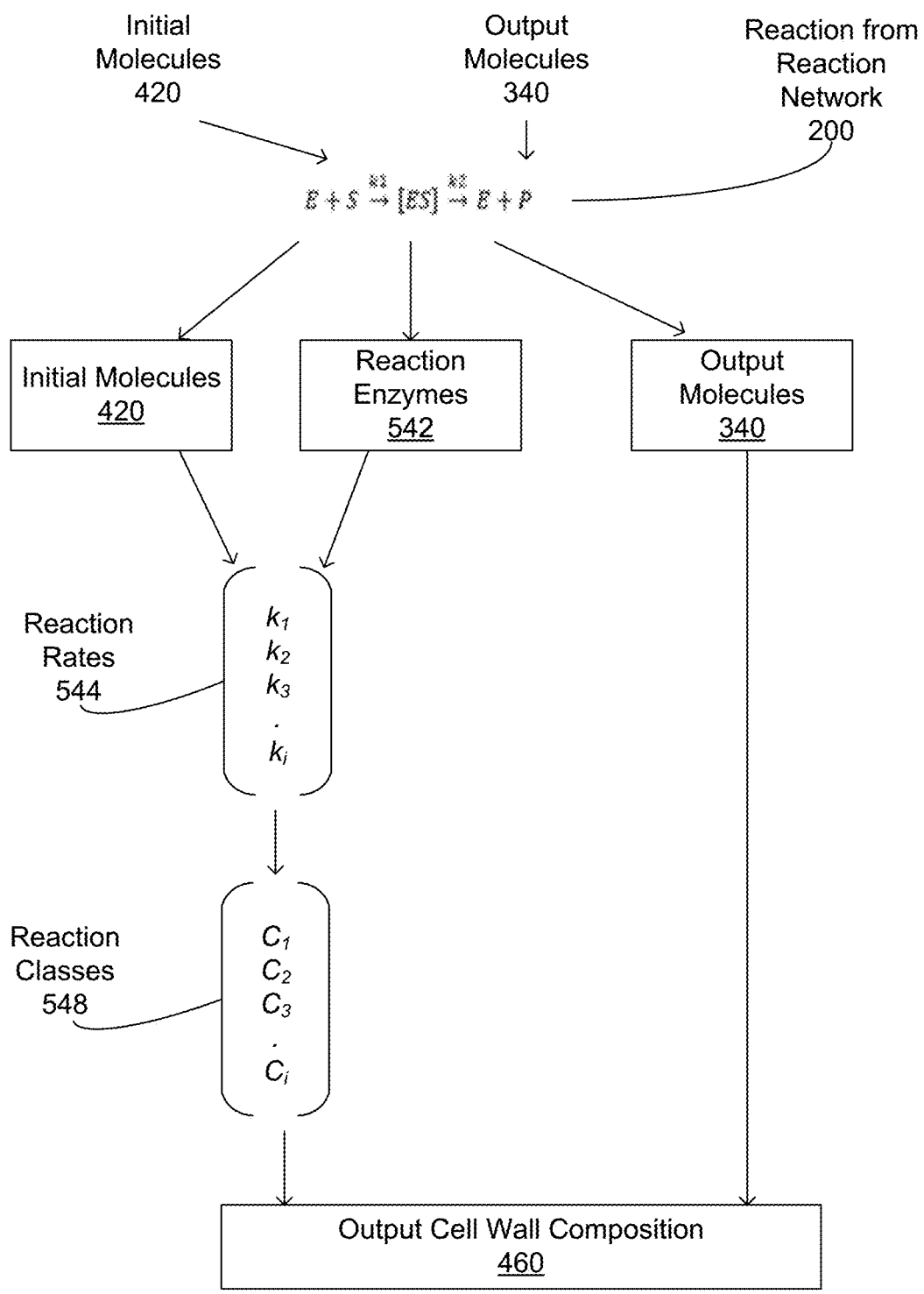
FIG. 5B is a graphical flow chart describing the logical operations of the long timescale model, according to an embodiment.
Figure 5C:
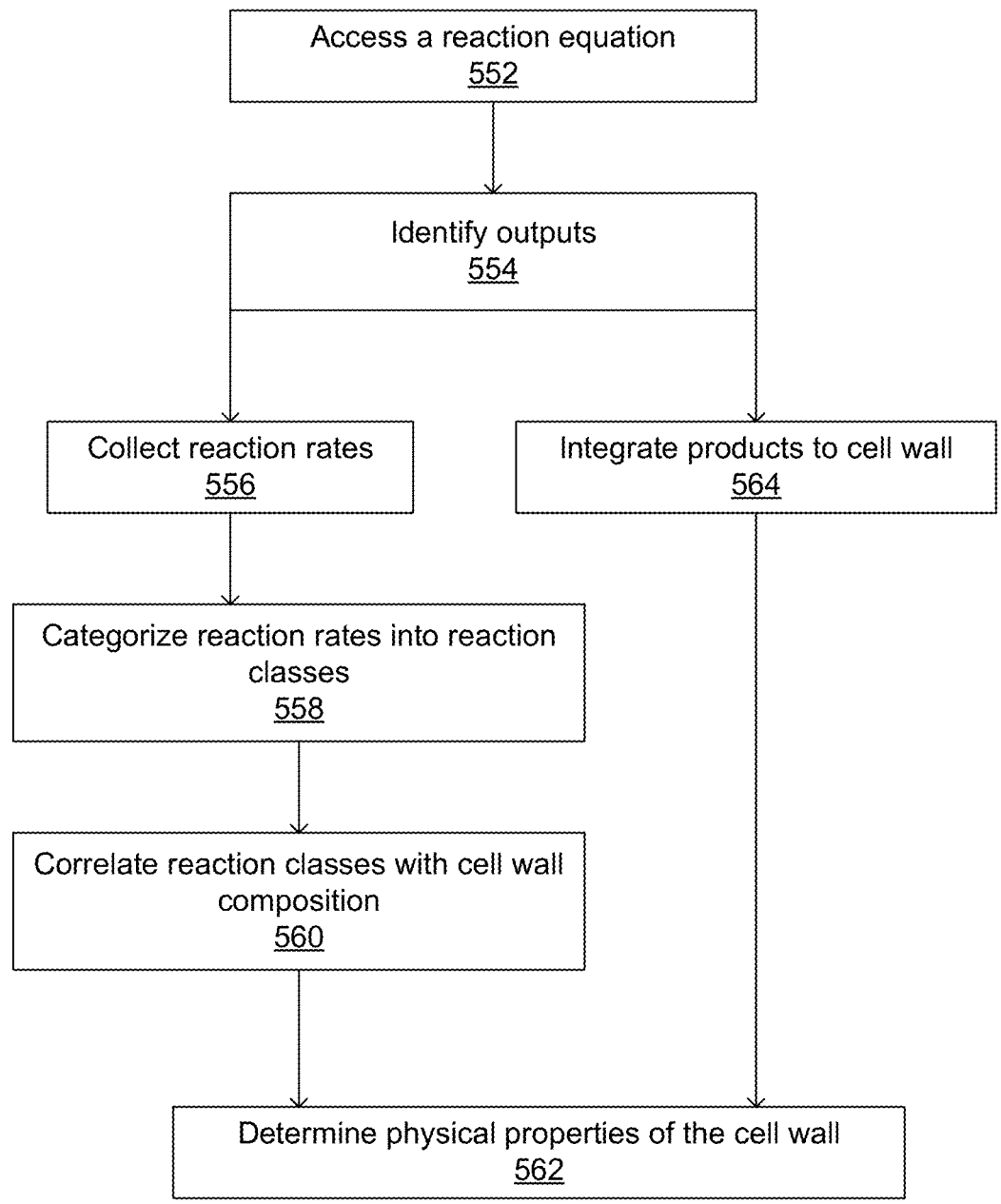
FIG. 5C is a flow chart for using the long timescale model to determine a relationship between the chemical composition and physical properties of the cell wall, according to an embodiment.

FIGS. 5B and 5C further illustrate the functionality of the logical structures of FIG. 5A. FIG. 5B is a graphical flow chart describing the logical operations of the long timescale model, according to an embodiment. FIG. 5C is a flow chart for using the long timescale model to determine a relationship between the chemical composition and physical properties of the cell wall, according to an embodiment. The chemical reaction module 505 receives an instruction to simulate reactions. For example the chemical reaction module 505 accesses 552 a reaction equation, in which the reactants E, and S are used as initial molecules 420 in a first forward reaction and form a reaction intermediate [ES]. The reaction intermediate [ES] further undergoes a second forward reaction to yield final products, output molecules 340, E and P. From the reaction, the chemical reaction module 505 identifies 554 the input molecules 420 and the output molecules 340 E and P, in this case molecules that are integrated 564 into the cell wall composition by module 515. The chemical reaction module 505 further identifies 554 the reaction enzymes 542 guiding the progress of the reaction. In one embodiment, the long timescale model 410 is deterministic such that the output molecules 340 are used directly by the cell wall composition module 515 to determine the output cell wall composition 340. Specifically, the output cell wall molecules 340 are analyzed by module 515 using the methods described above to determine how they affect the cell wall composition to generate the output cell wall composition 460.

In the same or a different embodiment, the long timescale model 410 is predictive such that the cell wall composition module 515 uses trends and/or classifications associated with the initial molecules 420 and reaction enzymes 542, and formed reaction classes 548 to estimate the output cell wall composition 460 without necessarily relying entirely on the output molecules 340. Explaining by way of the example of FIG. 5B, the first forward reaction proceeds at a reaction rate, $k_1$, and the second forward reaction proceeds at a reaction rate, $k_2$. The reaction rates $k_1$ and $k_2$ are collected 556 by the reaction classification module 510 and added to a set of reaction rates 544. The reaction classification module 510 uses the set of reaction rates 544 to categorize 558 similar reaction rates into one of a number of reaction classes 548.

By classifying all possible chemical reactions occurring in the cell wall at any given time, the long timescale model 410 can computationally estimate changes in the physical properties of the cell wall at any given composition. Alternatively, prior to simulating or receiving instructions for a chemical reaction, the model may classify reactions based on known cell properties and reaction conditions. In such an implementation, the long timescale model 410 may only receive a reaction class designation to estimate the chemical composition and physical properties of the cell wall. After updating the current output cell wall composition 460, the output cell wall composition is correlated 560 with the currently recorded reaction classes, to be referenced in future simulations.

The physical property analysis module 525 provides insight into the relationship between the chemical composition and the physical properties by converting the output cell wall composition 460 into physical properties of the cell wall 562.

VI. Short Timescale Model

The short timescale model 430 determine how the physical properties of the modeled cell as determined from the cell wall composition 460 may cause short timescale effects in other cell wall physical properties. One class of physical properties of interest are the failure conditions of the cell. In one embodiment, the short timescale model 430 assumes the internal conditions of the cell are at equilibrium and that certain conditions are fixed and uniform through the cell. Examples of these conditions include the chemical composition of the cell wall, the cell structure of the cell, the cell geometry, and the physical properties of the cell wall. Given these assumption, the short timescale model 430 manipulates specific physical properties, while approximating others as fixed, and generates conclusions regarding the conditions under which a cell may die. Cell death may be characterized as cell lysis, a lack of growth in a cell, or the failure of another function critical to a cell function.

Figure 6A:
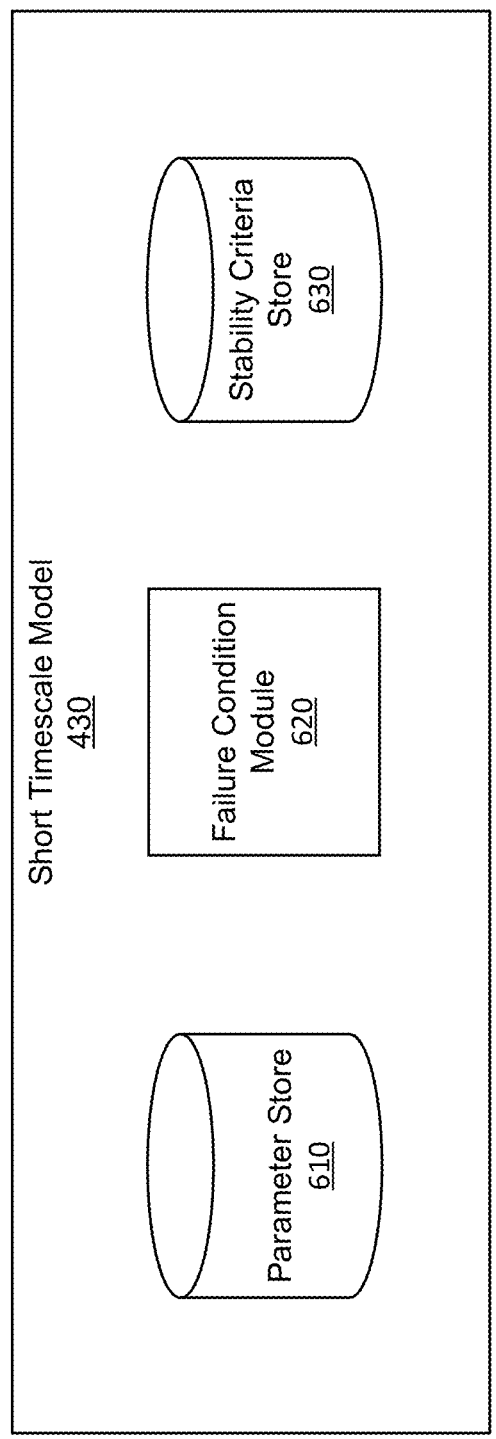
FIG. 6A is a block diagram illustrating the logical architecture of a short timescale model, according to an embodiment.

FIG. 6A is a block diagram illustrating the logical architecture of the short timescale model 430, according to an embodiment. In one embodiment, the short timescale model 430 comprises a function parameter store 610, a failure condition module 620, and a stability criteria store 630. In other embodiments, the short timescale model 430 may include more or fewer modules. Functionality indicated as being performed by a particular module may be performed by other modules instead.

Values for the physical properties 470, as determined by the output cell composition 460, are stored in the parameter store 610. The failure condition module 620 uses the values of the received physical parameters 460 while holding the remaining physical parameters 480 fixed and determines whether the investigated conditions would result in cell death. As introduced above, the failure condition module 620 may be implemented as a physics-based model, or another kind of model. The stability criteria store 630 stores whether or not the input physical properties 470 and fixed properties 480 resulted in cell death, and thus whether those properties represent a set of acceptable conditions within the cell.

In practice, the short timescale model 430 may implement other modules other than a failure condition module 620.

Figure 6B:
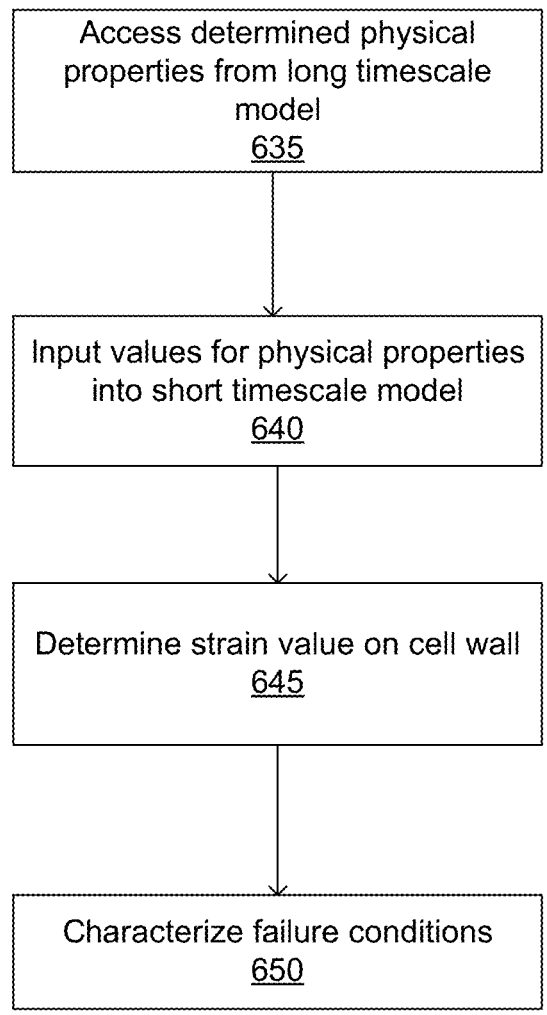
FIG. 6B is a flow chart describing the process for modelling short-term physical properties of the cell wall, according to an embodiment.

FIG. 6B is a flow chart describing the process for modelling short-term physical properties of the cell wall, according to an embodiment. The parameter store accesses 635 the determined physical properties 470 from the long timescale model 410 and inputs 640 the received values into a function stored within the short timescale model 430.

To characterize the physical integrity of the cell wall, the short time scale model 330 may manipulate one or more values of physical properties while approximating the remaining properties at fixed values. For example, the short timescale model 430 may investigate the stress-strain relationship of the cell wall given certain fixed physical properties. In the context of cell physics, stress here is a physical property that expresses the internal forces that neighboring particles of a continuous material (e.g., a cell wall) exert on each other and strain describes a measure of the deformation of the material. At equilibrium, the osmotic pressure exerted on the cell wall is met with an equivalent force exerted back by the cell wall to maintain the cell geometry. A common source of stress on the exterior of the cell is the osmotic pressure within the cell. Physically, as the osmotic pressure within the cell increases and exerts itself against the interior of the cell wall, greater stress and strain are exerted in the cell, resulting in the deformation of the cell. Cell deformation may result in a complete rupture in the cell wall or a multiple holes in the cell wall.

In one embodiment, the short timescale model 430 assumes a fixed cell geometry Examples of cell geometries that may be used include, but not limited to, a cylinder, a sphere, or a cylinder with spherical caps. As the cell moves away from equilibrium and osmotic pressure increases, the responsive force exerted by the cell wall is no longer equivalent. Osmotic pressure may increase due to the cell becoming hypertonic, or due to other causes.

The difference between the force due to osmotic pressure and the responsive force exerted by the cell wall causes the cell to stretch and deform, which may be computationally represented as the strain experienced by the cell wall. Chemically, the strain on the cell wall is characterized by the ability of the chemical bonds within the cell wall to resist the deformation. At a threshold strain, the chemical bonds break, resulting in holes within the cell wall or even the complete rupturing of the cell.

Figure 6C:
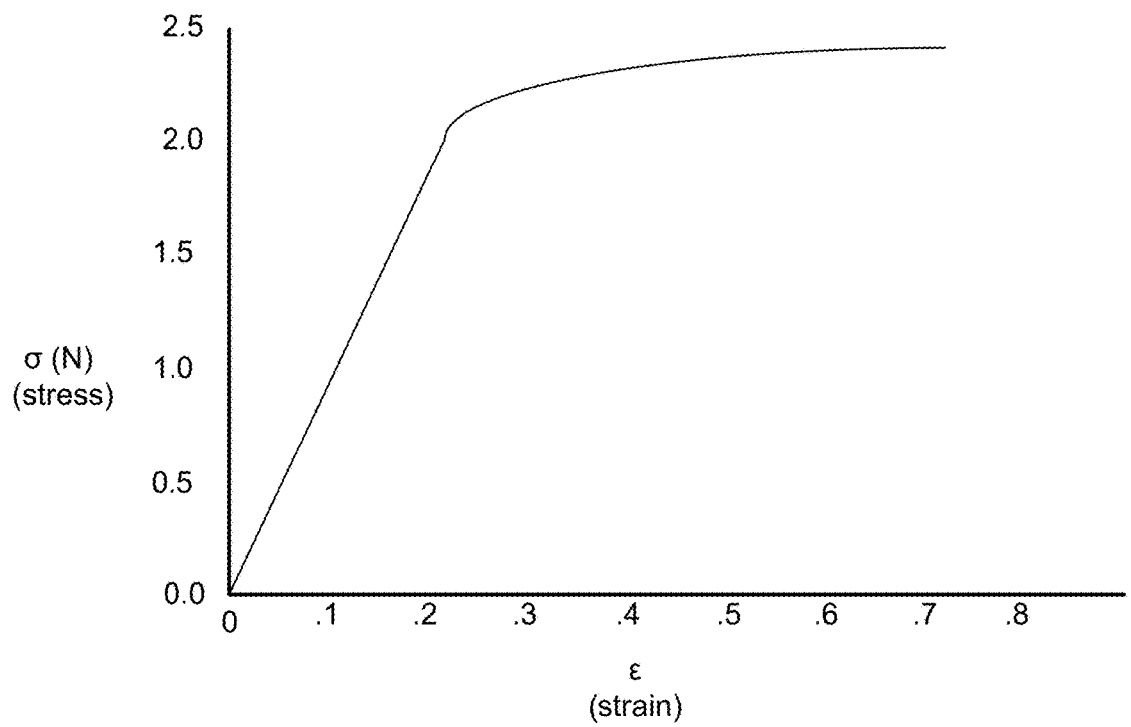
FIG. 6C illustrates an example relationship between the stress and strain experienced by the cell wall under various conditions, according to an embodiment.

In one embodiment, the short timescale model 430 determines 645 the maximum strain experienced by the cell wall. Mathematically, the stress and strain experienced by a material are directly proportional, related by a material-specific constant, Young's Modulus. FIG. 6C illustrates an example relationship between the stress and strain experienced by the cell wall, according to an embodiment. At a specific strain value, the cell wall experiences a maximum stress beyond which the cell will rupture and move towards death. The point of maximum stress and strain for a material is called the ultimate tensile strength. Any combination of stress and strain values below the ultimate tensile strength is stored within the stability criteria store 630 as a related to conditions at which the cell is capable of resisting the osmotic pressure within the cell.

The failure condition module 530 determines if the cell would experience failure conditions and characterizes 650 those failure conditions, as described above. Module 530 may accomplish this by evaluating the function of the short term model and comparing the result against previously determined failure conditions as stored in the stability criteria store 630. For example, for one or more simulations, the end output of the short term model 430 may be one or more resulting physical properties derived from the input physical properties 470, along with an estimation of the likelihood of whether those properties will result in a failure condition.

VII. Additional Considerations

A number of embodiments have been described. Nevertheless, it will be understood that various modifications may be made without departing from the spirit and scope of the invention.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method for improving efficiency of drug discovery, the method comprising:
   accessing a long timescale model of activity within a cell, the long timescale model characterizing a chemical composition of a cell wall of the cell based on a plurality of chemical reactions;
   accessing initial quantities of a set of input molecules that are reactants for the chemical reactions;
   evaluating the long timescale model with the initial quantities of the set of input molecules to determine a change in the chemical composition of the cell wall;
   determining a set of physical properties for the cell wall based on the change in the chemical composition of the cell wall;
   accessing a short timescale model of activity, the short timescale model characterizing a physical integrity of the cell wall;
   evaluating the short timescale model based on the physical properties of the cell wall to determine a strain on the cell wall;
   responsive to the strain indicating a threshold strain, detecting one or more failure conditions, the failure conditions representing lysis of the cell;
   facilitating a drug discovery process using the detection of the one or more failure conditions, wherein the facilitation includes identifying a drug-discovery target.

2. The method of claim 1, wherein the long timescale model describes the relationship between chemical composition of the cell wall and the physical properties of the cell wall.

3. The method of claim 1, wherein the chemical composition of the cell wall comprises at least one of:
   a number of cross-links between proteins of the cell wall;
   a chain length describing a number of molecules in the cell wall;
   a mass of the cell wall; and
   a thickness of the cell wall.

4. The method of claim 1, wherein the chemical composition of the cell wall comprises at least one of:
   presence of one or more molecules in the cell wall; and
   physical arrangement of one or more chemical constituents in the cell wall.

5. The method of claim 1, wherein the long timescale model is generated by experimentally varying the chemical composition of the cell wall and measuring the resulting physical properties.

6. The method of claim 1, wherein evaluating the long timescale model with the initial quantities of the set of input molecules to determine the change in the chemical composition of the cell wall comprises:
   accessing one or more chemical reactions occurring within the cell wall;
   integrating a set of outputs of the long timescale model into the chemical composition of the cell wall using the chemical reactions to determine the change in the chemical composition of the cell wall.

7. The method of claim 6, further comprising:
   classifying the chemical reactions into one of a plurality of reaction lists representing a class of reactant molecules; and
   integrating a set of outputs of the long time scale model into the chemical composition of the cell wall using the chemical reactions to determine the change in the chemical composition of the cell wall is further based on the lists associated with the chemical reactions.

8. The method of claim 1, wherein determining the physical properties of the cell wall is further based on at least one of:
   measurements by one or more mechanical sensors;
   data from a live cell, the data including a chemical composition of the cell wall and physical properties of the cell wall; and data from a live cell, the data including observations of changes in live cell geometry in fluids of different osmolarities.

9. The method of claim 1, wherein the one or more failure conditions comprise:
a rupture in the cell wall;
a hole in the cell wall;
an inability of the cell wall to grow; and
a death of the cell.

10. The method of claim 1, wherein the short timescale model describes the relationship between the physical properties of the cell wall.

11. The method of claim 1, wherein the short timescale model assumes steady-state conditions within the cell.

12. The method of claim 1, wherein the short timescale model specifies one of the following cell geometries:
a cylinder;
a cylinder with spherical caps;
a sphere; and
an ellipsoid.

13. The method of claim 1, wherein the short timescale model is a physics-based model that relates values for the physical properties for the cell wall determined based on the change in chemical composition of the cell wall to at least one output physical property.

14. The method of claim 13, wherein the physics-based model is further based on:
values for a set of fixed physical properties unaffected by the chemical composition of the cell wall.

15. The method of claim 13, wherein the short timescale model approximates one or more output physical properties comprising:
turgor pressure;
osmotic pressure;
mechanical stress;
mechanical strain; and
cell geometry.

16. The method of claim 13, wherein the short timescale model further comprises a set of stability criteria, the set of stability criteria describing conditions beyond which a cell experiences failure conditions.

17. The method of claim 16, wherein the set of stability criteria comprises a threshold osmotic pressure beyond which the chemical bonds of the cell wall break.

18. A non-transitory computer readable storage medium storing instructions that, when executed by a processor, cause the processor to perform a set of actions for improving efficiency of drug discovery, the set of actions comprising:
accessing a long timescale model of activity within a cell, the long timescale model characterizing a chemical composition of a cell wall of the cell based on a plurality of chemical reactions;
accessing initial quantities of a set of input molecules that are reactants for the chemical reactions;
evaluating the long timescale model with the initial quantities of the set of input molecules to determine a change in the chemical composition of the cell wall;
determining a set of physical properties for the cell wall based on the change in the chemical composition of the cell wall;
accessing a short timescale model of activity, the short timescale model characterizing a physical integrity of the cell wall;
evaluating the short timescale model based on the physical properties of the cell wall to determine a strain on the cell wall;
responsive to the strain indicating a threshold strain, detecting one or more failure conditions, the failure conditions representing lysis of the cell; and
facilitating a drug discovery process using the detection of the one or more failure conditions, wherein the facilitation includes identifying a drug-discovery target.

19. The non-transitory computer readable storage medium of claim 18, wherein evaluating the long timescale model with the initial quantities of the set of input molecules to determine the change in the chemical composition of the cell wall comprises:
accessing one or more chemical reactions occurring within the cell wall;
integrating a set of outputs of the long timescale model into the chemical composition of the cell wall using the chemical reactions to determine the change in the chemical composition of the cell wall.

20. A system comprising:
a processor; and
a non-transitory computer readable storage medium storing instructions that, when executed by a processor, cause the processor to perform a set of actions for improving efficiency of drug discovery, the set of actions comprising:
accessing a long timescale model of activity within a cell, the long timescale model characterizing a chemical composition of a cell wall of the cell based on a plurality of chemical reactions;
accessing initial quantities of a set of input molecules that are reactants for the chemical reactions;
evaluating the long timescale model with the initial quantities of the set of input molecules to determine a change in the chemical composition of the cell wall;
determining a set of physical properties for the cell wall based on the change in the chemical composition of the cell wall;
accessing a short timescale model of activity, the short timescale model characterizing a physical integrity of the cell wall;
evaluating the short timescale model based on the physical properties of the cell wall to determine a strain on the cell wall;
responsive to the strain indicating a threshold strain, detecting one or more failure conditions, the failure conditions representing lysis of the cell;
facilitating a drug discovery process using the detection of the one or more failure conditions, wherein the facilitation includes identifying a drug-discovery target.

* * * * *